United States Patent
D'Apuzzo et al.

(10) Patent No.: US 11,932,844 B2
(45) Date of Patent: *Mar. 19, 2024

(54) FLAT-FORM IMAGING FOR MICROSCOPIC OBJECTS

(71) Applicant: Hewlett-Packard Development Company, L.P., Spring, TX (US)

(72) Inventors: Fausto D'Apuzzo, Palo Alto, CA (US); Anita Rogacs, San Diego, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 441 days.

This patent is subject to a terminal disclaimer.

(21) Appl. No.: 17/256,333

(22) PCT Filed: Oct. 9, 2018

(86) PCT No.: PCT/US2018/054972
§ 371 (c)(1),
(2) Date: Dec. 28, 2020

(87) PCT Pub. No.: WO2020/076299
PCT Pub. Date: Apr. 16, 2020

(65) Prior Publication Data
US 2021/0222112 A1    Jul. 22, 2021

(51) Int. Cl.
| | |
|---|---|
| *C12M 1/34* | (2006.01) |
| *G02B 1/00* | (2006.01) |
| *G02B 1/06* | (2006.01) |
| *G02B 21/00* | (2006.01) |
| *G02B 21/06* | (2006.01) |
| *G02B 21/36* | (2006.01) |
| *G06V 20/69* | (2022.01) |

(52) U.S. Cl.
CPC ............. *C12M 41/36* (2013.01); *G02B 1/002* (2013.01); *G02B 1/06* (2013.01); *G02B 21/0004* (2013.01); *G02B 21/06* (2013.01); *G02B 21/364* (2013.01); *G02B 21/365* (2013.01); *G06V 20/693* (2022.01); *G02B 2207/101* (2013.01)

(58) Field of Classification Search
CPC ..... C12M 41/36; G06V 20/693; G02B 1/002; G02B 1/06; G02B 21/0004; G02B 21/06; G02B 21/364; G02B 21/365; G02B 2207/101

See application file for complete search history.

(56) References Cited

U.S. PATENT DOCUMENTS

| | | |
|---|---|---|
| 6,251,624 B1 | 6/2001 | Matsumura et al. |
| 7,145,645 B2 | 12/2006 | Blumenfeld et al. |

(Continued)

FOREIGN PATENT DOCUMENTS

| | | |
|---|---|---|
| EP | 3289333 | 3/2018 |
| RU | 2522005 C2 | 7/2014 |
| WO | WO-2018023039 A1 | 2/2018 |

*Primary Examiner* — Nicole M Ippolito
*Assistant Examiner* — Hanway Chang
(74) *Attorney, Agent, or Firm* — Foley & Lardner LLP

(57) ABSTRACT

An example apparatus includes a sampling layer to position microscopic objects thereon, a light encoding layer to encode light from passing through the microscopic objects of the sampling layer, the light encoding layer having a substantially flat form, and an imaging layer to capture an image of the sampling layer, the image being encoded by the light encoding layer.

15 Claims, 4 Drawing Sheets

(56) References Cited

U.S. PATENT DOCUMENTS

| | | | |
|---|---|---|---|
| 11,543,356 B2 * | 1/2023 | Shkolnikov | ............ C12M 23/12 |
| 2008/0186492 A1 | 8/2008 | Kiesel et al. | |
| 2012/0094323 A1 | 4/2012 | Dekker et al. | |
| 2017/0003491 A1 | 1/2017 | Waller et al. | |

* cited by examiner

FLAT-FORM IMAGING FOR MICROSCOPIC OBJECTS

BACKGROUND

Analysis of biological material, such as cells, is performed for a variety of applications. Analysis is often performed by isolating biological material, such as cells or type of cells, and taking an image of the biological material. The image may be taken using, for example, a microscope. The image may then be analyzed for identification or detection of various features of the biological material.

BRIEF DESCRIPTION OF THE DRAWINGS

For a more complete understanding of various examples, reference is now made to the following description taken in connection with the accompanying drawings in which.

DETAILED DESCRIPTION

As noted above, analysis of biological material often includes imaging of the biological material. Such imaging often results in imaging of a single sample or a small number of samples. Thus, monitoring of reactions, for example, may be limited to a few samples at any one time, resulting in long sample-to-result times. Further, imaging systems are often large due to the desired amplification of the samples. For example, a microscope with a long focal length may be employed to image a microscopic sample.

In various examples, cells in a well plate with multiple wells may be imaged or monitored with a flat-form imaging arrangement. In one example, the well plate is provided with a light source on one side (e.g., above the well plate)) to illuminate the cells in the wells of the well plate. On the other side of the well plate (e.g., below the well plate), a light encoding layer and an imaging layer are provided. The light imaging layer may be a lens-less layer to provide computational imaging. In this regard, the computational imaging may be achieved with an amplitude mask or a diffuser. In other examples, the light imaging layer may include a flat-lens array (e.g., meta-lens array). The light encoding layer may encode the light from the light source passing through the cells in the well plate. The raw imaging data may be captured by the imaging layer, which may include a CCD or a CMOS layer. The use of a flat-form light encoding layer provides a large field of view for the imaging layer, allowing simultaneous imaging or monitoring of a well plate with a large number of wells.

Referring now to the Figures, a cross-sectional side view of an example apparatus 100 for flat-form imaging is illustrated. The example apparatus includes a sampling layer 110 to position microscopic objects 112 thereon. In various examples, the microscopic objects 112 may be positioned on a surface of the sampling layer 110 in a variety of manners, examples of which are described below with reference to FIGS. 2 and 3. The sampling layer 110 may be formed of any of a variety of materials such as, for example, plastics or glasses. In one example, the sampling layer 110 is formed of a non-reactive material, such as polypropylene. The sampling layer 110 may be of any practical size according to a desired application. For example, the sampling layer 110 may be sized to accommodate a specific number of microscopic objects 112. The microscopic objects 112 may include any of a variety of objects such as cells or biological reagents, for example.

In various examples, the sampling layer 110 is provided with a cell immobilization layer, as described below with reference to FIG. 3. The cell immobilization layer can facilitate positioning of the microscopic objects 112 on the surface of the sampling layer 110.

Figure 1:
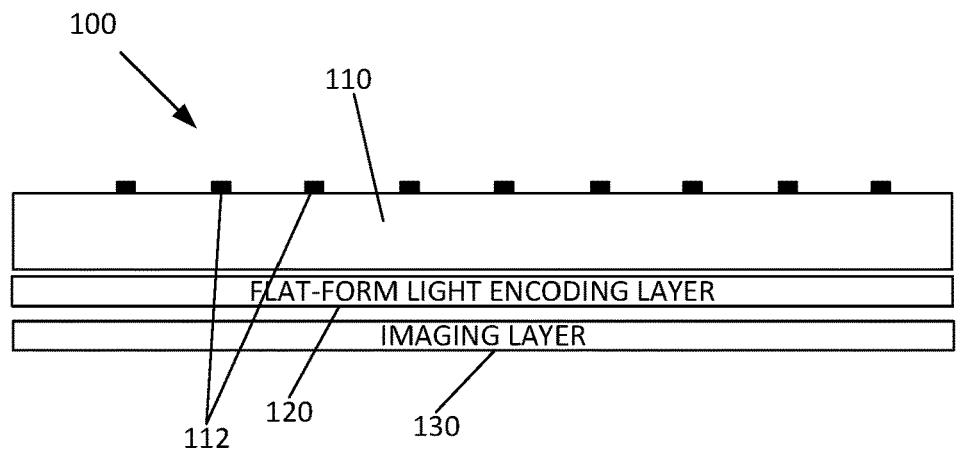
FIG. 1 is a cross-sectional side view of an example apparatus for flat-form imaging.

The example apparatus 100 of FIG. 1 is provided with a light encoding layer 120. The light encoding layer 120 of the example apparatus 100 has a substantially flat form. For example, the light encoding layer may include a flat-form, lens-less computational imaging layer which may include an amplitude mask or a diffuser, as described below with reference to FIG. 4, or a substantially flat array of lenses (e.g., meta-lens array), as described below with reference to FIG. 5. The flat-form nature of the light encoding layer 120 facilitates a wide field of view which can allow encoding of light over a large area simultaneously. In this regard, light passing through a large number of microscopic objects 112 on a relatively large area of the sampling layer 110 can be simultaneously encoded.

The example apparatus 100 of FIG. 1 further includes an imaging layer 130 to capture an image encoded by the light encoding layer 120. As noted above, the image encoded by the light encoded layer 120 is encoding of light passing through the sampling layer 110 and any microscopic objects 112 on the sampling layer 110. In this regard, the imaging layer 130 is able to capture an image of a wide field of view, as encoded by the light encoding layer 120. In various examples, the imaging layer may include a charge-coupled device (CCD) or a complementary metal-oxide semiconductor (CMOS) device, for example. Thus, the example apparatus 100 is able to image a wide field of view with a flat form.

Figure 2:
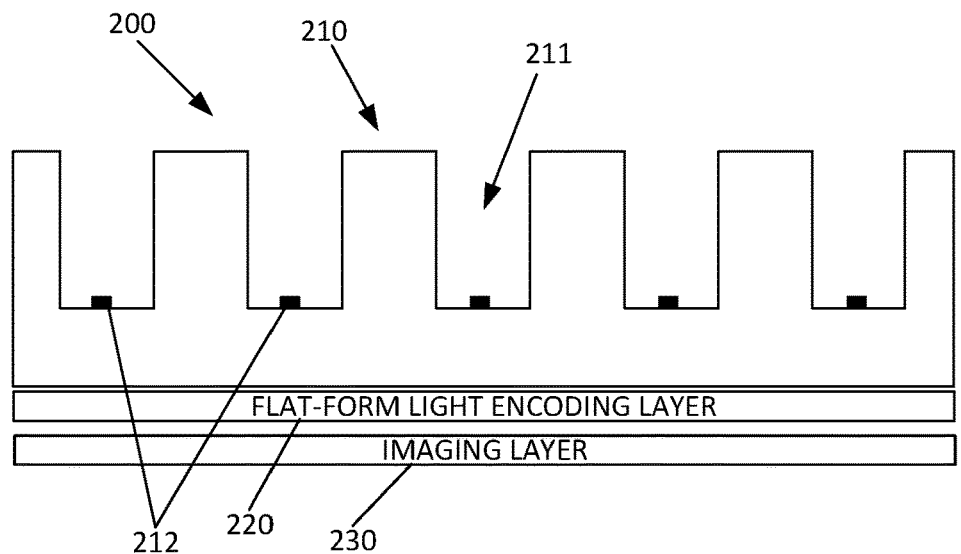
FIG. 2 is a cross-sectional side view of another example apparatus for flat-form imaging.

The positioning of the microscopic objects 112 on the sampling layer 110 may be facilitated by any of a variety of manners. FIGS. 2 and 3 illustrate two such examples.

Referring first to FIG. 2, a cross-sectional side view of another example apparatus 200 for flat-form imaging is illustrated. The example apparatus 200 is similar to the example apparatus 100 of FIG. 1 and includes a sample layer 210, a flat-form light encoding layer 220 and an imaging layer 230. The flat-form light encoding layer 220 and the imaging layer 230 may be similar to the light encoding layer 120 and the imaging layer 130, respectively, of the example apparatus 100 of FIG. 1.

In the example apparatus 200 of FIG. 2, the sampling layer 210 includes an array of wells 211 formed to position microscopic objects 212 within the various wells 211. In various examples, the sample layer 210 may include any number of wells 211. In the example of FIG. 2, each well 211 is defined by at least one side wall and a bottom floor. The size and shape of each well 211 may be selected from any of a variety of sizes and shapes. In one example, as illustrated in FIG. 2, the wells 211 are cylindrical with a cross section that may be circular, rectangular, hexagonal or any of a variety of other shapes. In other examples, each well 211 is conical or other non-cylindrical shape. In one example, each well 211 is a circular cylinder with a diameter of between 1 mm and 100 mm.

Figure 3:
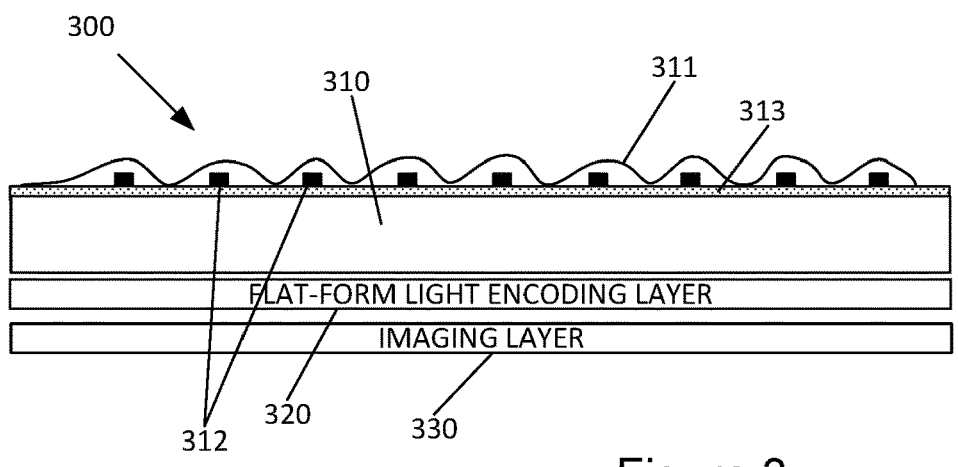
FIG. 3 is a cross-sectional side view of another example apparatus for flat-form imaging.

Referring now to FIG. 3, a cross-sectional side view of another example apparatus 300 for flat-form imaging is illustrated. The example apparatus 300 is similar to the example apparatus 100 of FIG. 1 and includes a sample layer 310, a flat-form light encoding layer 320 and an imaging layer 330. The flat-form light encoding layer 320 and the imaging layer 330 may be similar to the light encoding layer 120 and the imaging layer 130, respectively, of the example apparatus 100 of FIG. 1.

In the example apparatus 300 of FIG. 3, the sampling layer 310 includes a material 311 to accommodate solid phase cell culturing in discrete positions. For example, the material 311 may include an agar gel which facilitates holding microscopic objects 312 in a desired position.

In various examples, the sampling layer 310 may be provided with an immobilization layer 313 to facilitate positioning of the microscopic objects. In various examples, the immobilization layer 313 may include an agar substrate to facilitate attachment of the microscopic objects. In other examples, an electrical field may be generated by an alternating current (AC) applied to electrodes formed on the sampling layer 310 may be used to direct the objects to a surface of the sampling layer 310. In this regard, the immobilization layer 313 may include an array of electrodes coupled to an AC power source.

Figure 4:
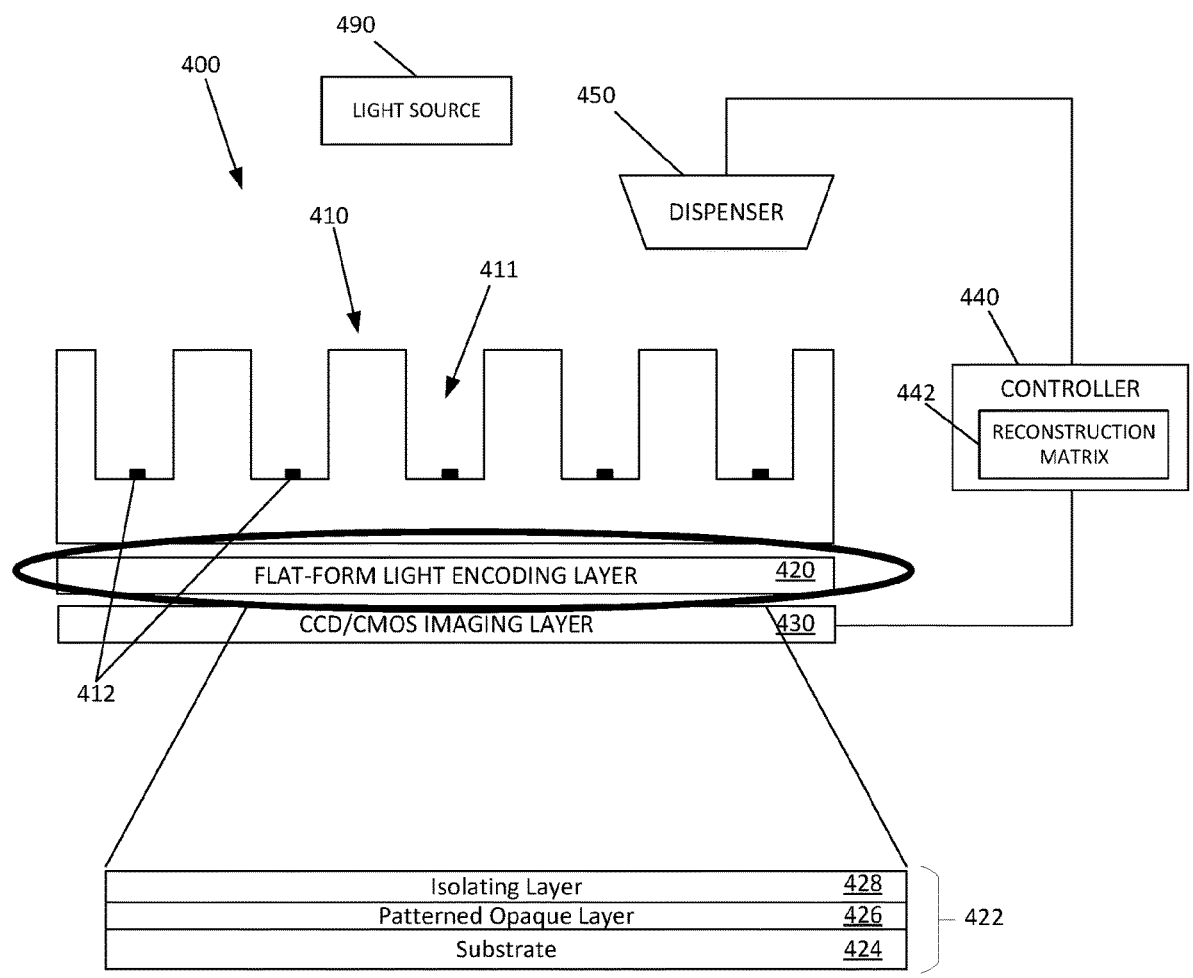
FIG. 4 is a schematic illustration of an example system for flat-form imaging.

Referring now to FIG. 4, a schematic illustration of an example system 400 for flat-form imaging is illustrated. The example system 400 includes a sampling layer in the form of a well plate 410. The well plate 410 of the example system 400 includes at least one well 411. The well plate 410 may be formed of any of a variety of materials such as, for example, plastics or glasses. In one example, the well plate 410 is formed of a non-reactive material, such as polypropylene. The well plate 410 may be of any practical size according to a desired application. For example, the well plate 410 may be sized to accommodate a specific number of wells 411.

In various examples, the well plate 410 of the example system 400 may be provided with any number of wells 411. The size and shape of each well 411 may be selected from any of a variety of sizes and shapes. In one example, the well 411 is cylindrical with a cross section that may be circular, rectangular, hexagonal or any of a variety of other shapes. In other examples, the well 411 is conical or other non-cylindrical shape. In one example, the well 411 is a circular cylinder with a diameter of between 1 mm and 100 mm.

Each well 411 may be provided for positioning of microscopic objects 412 therein. As noted above, the microscopic objects 412 may include biological material such as cells, for example. The wells 411 are formed to allow positioning of the microscopic objects 412 at or near a bottom surface of the well 411 to facilitate imaging of the microscopic objects 412 from beneath the sampling layer 410.

The example system 400 of FIG. 4 is provided with a light encoding layer 420 positioned below the well plate and an imaging layer 430 positioned below the light encoding layer 420. A light source 490 is positioned above the sampling layer 410 to illuminate the sampling layer 410. Thus, the light source 490 is positioned on one side of the sampling layer 410, and the light encoding layer 420 and the imaging layer 430 are positioned on a second, opposite side of the sampling layer 410.

Thus, the light encoding layer 420 is positioned to encode light from the light source 490 passing through the array of wells 411, as well as any microscopic objects 412 therein. As noted above, in various example, the light encoding layer 420 is provided with a substantially flat form.

In one example, the flat-form light encoding layer 420 includes a lens-less, amplitude mask arrangement 422, as illustrated in the example of FIG. 4. The amplitude mask arrangement 422 is provided to encode the light passing through the sampling layer 410 for computational reconstruction of the encoded information. The amplitude mask arrangement 422 includes a substrate 424 to support a patterned opaque layer 426 and an isolating layer 428. Light passing through the sampling layer 410 is passed through the isolating layer 428 and onto the patterned opaque layer 426.

As noted above, the amplitude mask arrangement 422 can facilitate computational imaging. In this regard, computational imaging uses conversion of the incident light to sensor measurements. Rather than representing an image, the sensor measurements can be coupled with an appropriate algorithm or function to reconstruct an image. The algorithm or function may be determined through a calibration process.

In various examples, the amplitude mask arrangement 422 may be directly coupled to the well plate 410. For example, the amplitude mask arrangement 422 may form the bottom surface of the well plate 410. In this regard, the isolating layer 428 may serve to facilitate adhesion of microscopic objects (e.g., cells) by providing isolation (e.g., chemical isolation) between the microscopic objects and the patterned opaque layer 426. Such isolation may prevent the microscopic objects from being affected by, for example, metals in the patterned opaque layer 426 which may be toxic to the microscopic objects.

The patterned opaque layer 426 is provided with different regions to allow light of different amplitudes or wavelengths to pass through. The pattern of regions on the patterned opaque layer 426 is a two-dimensional separable pattern to encode the light in 2-dimensional pixels. In this regard, the pattern is separated into regions, where each region may correspond to a pixel in the captured image. Each region may be sized to provide a resolution in the captured image of between 3 microns and 100 microns. Thus, the light encoded by the amplitude mask arrangement 422 may be captured by the imaging layer 430 in the form of an M×N matrix of pixels, each pixel being between 3 microns and 100 microns wide. In various examples, the imaging layer 430 may include a CCD layer or a CMOS layer. As noted above, the pattern allows for a computational conversion of the encoded light to an image through an appropriate algorithm or function. Thus, the exact pattern formed on the patterned opaque layer 426 may be any feasible pattern.

In one example, the patterned opaque layer 426 is formed with a fused silica glass wafer with a thin film of chromium deposited thereon. The chromium is etched to form a pattern. In various example, the pattern is formed to provide a desired feature size which can correspond to a pixel in the imaging layer 430.

In some examples, the amplitude mask arrangement 422 may be replaced with a diffuser layer (not shown). The diffuser layer may include a layer of a material with a non-uniform optical density, such as a thin sheet of thermally cured polymer or any semi-transparent coating. Various examples of diffuser layers may be fabricated with cost-efficient methods, such as fiber deposition, spin-coating or the like. Such methods can achieve the desired result without the use of specialized equipment such as for photolithography. The non-uniform density of the diffuser layer can allow encoding of light which can be processed to produce a reconstructed image using, for example, a reconstruction matrix 442, as described below.

The image captured by the imaging layer 430 may be processed by a controller 440 coupled to the imaging layer 430. In various examples, the controller 440 may include a processor to execute various instructions. The controller 440 may be implemented as hardware, software, firmware, or a combination thereof. In one example, the controller 440 is implemented as software stored on a non-transitory computer-readable medium and includes instructions that may be executable by a processor.

The processing of the image from the imaging layer 430 may include translating the raw image from the imaging layer 430 by a reconstruction matrix 442. The reconstruction matrix 442 may be obtained through calibration of the light encoding layer 420, for example. Thus, an array of pixels from the imaging layer 430 representing the raw image may be multiplied by the reconstruction matrix 442 to obtain an array of pixels representing a reconstructed image. Thus, the flat-form light encoding layer 420 can facilitate imaging of a wide field of view simultaneously.

In the example system 400 of FIG. 4, the controller 440 is coupled to a dispenser 450. The dispenser 450 is provided to drop, or inject, objects such as cells into the various wells 411 of the well plate 410. In various examples, the dispenser 450 may be provided to drop a single cell at a time. The controller 450 may be coupled to the dispenser 550 to move the dispenser to a selected location corresponding to a selected well 411. In other examples, the system 400 may include a movable stage (not shown) supporting the well plate 410. In this regard, the controller 440 may coordinate movement of the movable stage and the timing of dropping of the cell from the dispenser 450 to drop the cell into a desired, or selected, well 411 in the well plate 410

In some examples, the dispenser 450 may inject or drop additional material into the wells 411. For example, the dispenser 450 may be used to add stimuli onto cells already in the wells 411 to facilitate a reaction or other response that may be observed or imaged. In other examples, the dispenser 450 may add fluorescent dyes or other stains to facilitate the imaging.

Thus, as noted above, the example system 400 may be used to facilitate imaging of a wide field of view simultaneously. The wide field of view may include a large number of wells 411 of the well plate 410, for example, thus allowing various types of analyses.

In one example, a large number of different reactions may be simultaneously monitored. For example, different combinations of drugs or concentrations of drugs may be provided in the various wells 411, or onto an immobilization layer. The wide field of view allows the progress of reactions to be simultaneously monitored. In this regard, the light encoding layer 420 and the imaging layer 430 may generate raw image data at regular intervals. The controller 440 may then process the raw image data using the reconstruction matrix 442. The reconstructed images from the various wells 411 may then be used to monitor reactions in the various wells 411. The monitoring of a large number of wells 411 and reactions in those wells 411 can substantially reduce the time to obtain reaction results and facilitate rapid identification of a viable drug combination, for example.

In other examples, the large field of view may be used to simultaneously monitor culture growth for a large number of samples. For example, the various wells 411 of the well plate 410 may be provided with different antibiotic combinations, cells, nutrients, or other material. The growth of culture in the wells 411 within the large field of view may then be imaged using the flat-form light encoding layer 420 and the imaging layer 430. Again, the images may be captured at regular intervals, allowing evaluation of growth rates of cultures in the different wells 411. Evaluation of the growth rates in the large number of samples using the large field of view allows rapid identification of, for example, an effective antibiotic.

Figure 5:
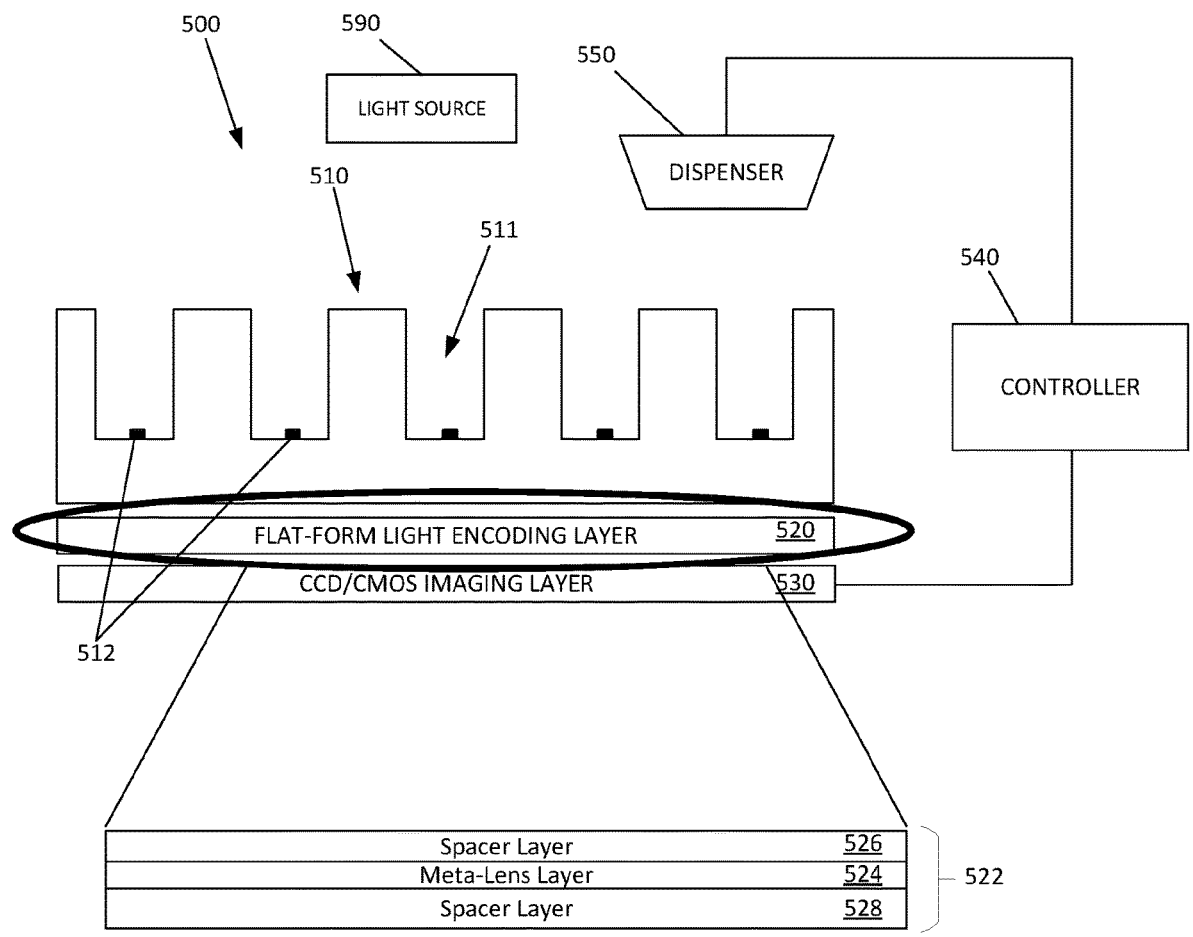
FIG. 5 is a schematic illustration of an example system for flat-form imaging.

Referring now to FIG. 5, a schematic illustration of another example system 50 for flat-form imaging is illustrated. The example system 500 of FIG. 5 is similar to the example system 400 described above with reference to FIG. 4 and includes a well plate 510 with various wells 511 to position microscopic objects 512, a light encoding layer 520, an imaging layer 530, a controller 540, a dispenser 550 and a light source 590.

In the example system 500 of FIG. 5, the light encoding layer 520 is meta-lens arrangement 522. The meta-lens arrangement 522 includes a meta-lens layer 524 formed with an array of substantially flat lenses. In various examples, the array of lenses may be formed in a grid pattern corresponding to a grid of pixels in an image. In one example, the lenses in the meta-lens layer 524 are circular lenses with a diameter of between about 5 microns and about 200 microns. The thickness of each lens and the meta-lens layer 524 is between about 100 nm and about 10 microns. In various examples, the meta-lens layer 524 is provided with spacer layers 526, 528 to properly position the array of meta-lenses relative to the microscopic objects 512. For example, the spacer layers 526, 528 may provide the desired working distance for the meta-lenses in the layer 524.

In one example, the flat lenses of the meta-lens layer 524 may be lenses with a high numerical aperture in the visible wavelengths. In this regard, the lenses may have diffractive properties which provide a designed or desired focal length. In other examples, the flat lenses are formed as transmissive dielectric metalenses. Such metalenses may be formed with $TiO_2$ nanofins formed on a glass substrate, as described in Khorasaninejad, Mohammadreza et al. (Jun. 3, 2016) Metalenses at visible wavelengths: Diffraction-limited focusing and subwavelength resolution imaging. *Science Magazine*, Pages 1190-1194.

The meta-lens arrangement 522 may thus encode light from the light source 590 passing through the well plate 510. Each meta-lens in the meta-lens layer 524 may correspond to a group of pixels in an image captured by the imaging layer 530. The controller 540 can assemble the complete image with image pixels from the imaging layer 530.

Thus, the light encoding layer 520 with the meta-lens layer 524 provides flat-form imaging with a wide field of view. As described above with respect to FIG. 4, the example system 500 may thus be used to simultaneously monitor a large number of samples for reactions or culture growth, for example.

Figure 6:
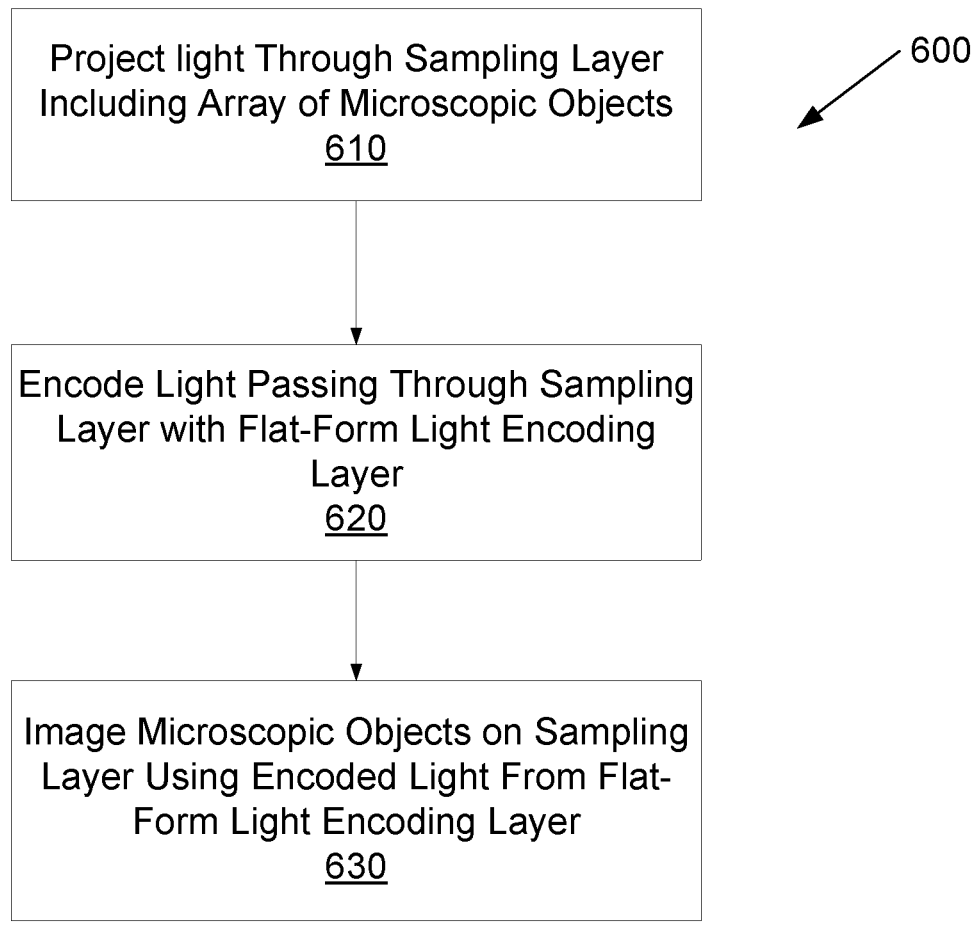
FIG. 6 is a flow chart illustrating an example method for flat-form imaging.

Referring now to FIG. 6, a flow chart illustrates an example method 600 for flat-form imaging. The example method 600 includes projecting light through a sampling layer having microscopic objects positioned thereon (block 610). As noted above, in various examples, the sampling layer may be a well plate with an array of wells, as described above with reference to FIG. 2, or a layer with a material, such as agar gel, to accommodate solid phase cell culturing in discrete positions, as described above with reference to FIG. 3. The positioning of the microscopic objects may be facilitated by a cell immobilization layer.

The example method further includes encoding light passing through the sampling layer with a substantially flat-form light encoding layer (block 620). In various examples, the light encoding layer may include an amplitude mask arrangement, as described above with reference to FIG. 4, or a meta-lens arrangement, as described above with reference to FIG. 5, for example. The flat-form encoding layer provides a large field of view to facilitate encoding of light passing through a large number of samples, for example.

The example method further includes imaging the microscopic objects on the sampling layer using encoded light from the flat-form light encoding layer (block 630). As noted above, a CCD device or a CMOS device may be used to capture an image using the encoded light from the flat-form light encoding layer.

Thus, the example systems described above provide an efficient and cost-effective imaging of a large number of samples. The use of flat-form light encoding allows imaging within a large field of view, allowing the large number of samples to be simultaneously monitored.

The foregoing description of various examples has been presented for purposes of illustration and description. The foregoing description is not intended to be exhaustive or limiting to the examples disclosed, and modifications and variations are possible in light of the above teachings or may be acquired from practice of various examples. The examples discussed herein were chosen and described in order to explain the principles and the nature of various examples of the present disclosure and its practical application to enable one skilled in the art to utilize the present disclosure in various examples and with various modifications as are suited to the particular use contemplated. The features of the examples described herein may be combined in all possible combinations of methods, apparatus, modules, systems, and computer program products.

It is also noted herein that while the above describes examples, these descriptions should not be viewed in a limiting sense. Rather, there are several variations and modifications which may be made without departing from the scope as defined in the appended claims.

What is claimed is:

1. An apparatus, comprising:
a sampling layer to position microscopic objects thereon;
a light encoding layer to encode light from passing through the microscopic objects of the sampling layer, the light encoding layer having a substantially flat form; and
an imaging layer to capture an image of the sampling layer, the image being encoded by the light encoding layer.

2. The apparatus of claim 1, further comprising:
a light source positioned on a first side of the sampling layer to illuminate the sampling layer,
wherein the light encoding layer is positioned on a second side of the sampling layer, the second side being opposite the first side.

3. The apparatus of claim 1, wherein the substantially flat form of the light encoding layer provides a wide field of view to encompass the microscopic objects on the sampling layer.

4. The apparatus of claim 1, wherein the sampling layer includes an array of wells.

5. The apparatus of claim 1, wherein sampling layer includes a material to accommodate solid phase cell culturing in discrete positions.

6. The apparatus of claim 1, wherein the light encoding layer includes a flat-form, lens-less computational imaging layer.

7. The apparatus of claim 6, wherein the flat-form computational imaging layer includes at least one of an amplitude mask or a diffuser.

8. The apparatus of claim 1, wherein the light encoding layer includes a substantially flat array of lenses.

9. The apparatus of claim 1, wherein the imaging layer includes at least one of a charge-coupled device (CCD) or a complementary metal-oxide semiconductor (CMOS) device.

10. A system, comprising:
a well plate including an array of wells;
a light encoding layer positioned below the well plate, the light encoding layer to encode light passing through the array of wells, the light encoding layer having a substantially flat form;
an imaging layer to capture the encoded image from the light encoding layer; and
a controller to generate a reconstructed image based on the encoded image.

11. The system of claim 10, further comprising:
a dispenser to dispense samples into the array of wells.

12. The system of claim 10, wherein the controller is to generate the reconstructed image via application of at least one reconstruction matrix to the encoded image.

13. The system of claim 10, wherein the controller is to monitor growth of samples in the array of wells.

14. A method, comprising:
projecting light through a sampling layer, the sampling layer including microscopic objects;
encoding the light passing through the sampling layer with a substantially flat-form light encoding layer; and
imaging the microscopic objects on the sampling layer using encoded light from the flat-form light encoding layer.

15. The method of claim 14, wherein the substantially flat-form light encoding layer provides a wide field of view to encompass the microscopic objects on the sampling layer.

* * * * *